United States Patent [19]

Müller et al.

[11] 4,269,788
[45] May 26, 1981

[54] PHENYL-CYCLOHEXADIENE-ALKYLAMINE DERIVATIVES

[75] Inventors: Peter M. Müller, Arlesheim; Rudolf Pfister; René Urban, both of Basel, all of Switzerland

[73] Assignee: Hoffmann-La Roche Inc., Nutley, N.J.

[21] Appl. No.: 81,712

[22] Filed: Oct. 4, 1979

[30] Foreign Application Priority Data

Oct. 11, 1978 [CH] Switzerland .................. 10552/78

[51] Int. Cl.³ ............................................. C07C 91/16
[52] U.S. Cl. .......................... 260/501.1; 260/459 R; 260/465 R; 424/316; 424/330; 560/102; 564/161; 564/218; 564/303; 564/304; 564/305; 564/496; 564/510; 568/320; 568/329; 568/715
[58] Field of Search .............. 260/570.5 CA, 570.8 R; 424/330

[56] References Cited

U.S. PATENT DOCUMENTS

| | | | |
|---|---|---|---|
| 3,320,283 | 5/1967 | Godefroi | 260/570.5 X |
| 3,520,931 | 7/1970 | d'Ostrowick et al. | 260/570.8 |
| 3,864,391 | 2/1975 | Borazin et al. | 260/570.5 |
| 3,928,603 | 12/1975 | Morean et al. | 260/570.8 X |

OTHER PUBLICATIONS

Barltrop, "Pure and Applied Chemistry", vol. 33, No. 2-3, (1973) p. 185.

*Primary Examiner*—Robert V. Hines
*Attorney, Agent, or Firm*—Jon S. Saxe; Bernard S. Leon; William G. Isgro

[57] ABSTRACT

Cyclohexadiene derivatives of the formula

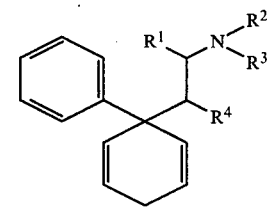

I wherein $R^1, R^2, R^3$ and $R^4$ are as hereinafter set forth, are described. The compounds of formula I are useful as analgesic agents.

4 Claims, No Drawings

PHENYL-CYCLOHEXADIENE-ALKYLAMINE DERIVATIVES

BRIEF SUMMARY OF THE INVENTION

The invention relates to cyclohexadiene derivatives of the formula

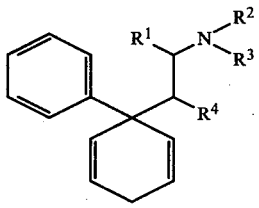

I wherein $R^1$ is hydrogen or methyl, $R^2$ is hydrogen, methyl or ethyl, $R^3$ is methyl or ethyl and $R^4$ is hydrogen or methyl; provided that at least one of $R^1$ and $R^4$ is hydrogen, (including the optically active antipodes of those compounds which have an asymmetric carbon atom), and pharmaceutically acceptable acid addition salts thereof.

DETAILED DESCRIPTION OF THE INVENTION

The cyclohexadiene derivatives of the invention are compounds of the formula

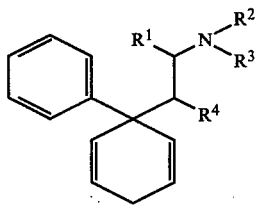

I wherein $R^1$ is hydrogen or methyl, $R^2$ is hydrogen, methyl or ethyl, $R^3$ is methyl or ethyl and $R^4$ is hydrogen or methyl; provided that at least one of $R^1$ and $R^4$ is hydrogen, pharmaceutically acceptable acid addition salts thereof, or the optically active antipodes of those compounds which have an asymmetric carbon atom.

The invention comprises the cyclohexadiene derivatives aforesaid, that is, the compounds of formula I, including their optical antipodes, and acid addition salts thereof; the preparation of these derivatives; pharmaceutical preparations containing these derivatives; and the preparation of said pharmaceutical preparations as well as the use of these derivatives or of pharmaceutical preparations containing these derivatives in the control of pains.

In accordance with the invention, the cyclohexadiene derivatives, that is, the compounds of formula I and their acid addition salts, are prepared by (a) reacting biphenyl in the presence of lithium or calcium and ammonia with a compound of the formula

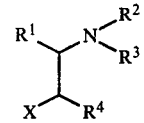

II wherein $R^1$, $R^2$, $R^3$ and $R^4$ are as previously described, and X is a leaving group, the compound of formula II is optionally used in the form of an optical antipode and/or an acid addition salt, or (b) reacting a compound of the formula

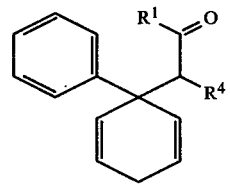

III wherein $R^1$ and $R^4$ are as previously described, under reducing conditions with an amine of the formula

IV wherein $R^2$ and $R^3$ are as previously described, or (c) reacting a compound of the formula

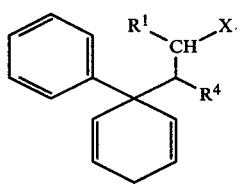

V wherein $R^1$, $R^4$ and X are as previously described, with an amine of formula IV, or (d) appropriately alkylating an amine of the formula

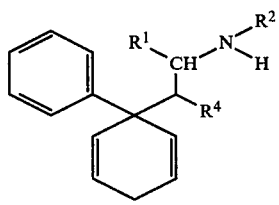

VI wherein $R^1$, $R^2$ and $R^4$ are as previously described, or (e) reducing an amide of the formula

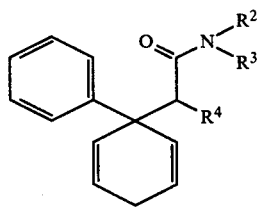

VII wherein $R^2$, $R^3$ and $R^4$ are as previously described, whereupon, if desired, a racemate obtained is resolved into its optically active antipodes and a product obtained is converted into a pharmaceutically acceptable acid addition salt, if desired.

The reaction according to process embodiment (a) is conveniently carried out in a solvent such as ether, tetrahydrofuran, monoglyme, diglyme or dioxane at a temperature in the range of from −80° C. to −30° C. Exemplary of the leaving group denoted by X are bromine, iodine, mesyl, tosyl, or the like; preferred is chlorine.

The reaction according to process embodiment (b) is preferably carried out in the presence of a solvent, for example, a lower alkanol, such as methanol, ethanol and isopropanol, at a temperature in the range of from −10° C. to 50° C. A borohydride, such as sodium cyanoborohydride or sodium borohydride can be used as the reducing agent.

The reaction according to process embodiment (c) is preferably carried out in an inert organic solvent such as, for example, toluene, benzene, xylene, monoglyme or diglyme, at a temperature in the range of from 120° C. to 180° C. The reaction is preferably carried out under pressure, for example, at 10 to 40 atmospheres. The leaving group denoted by X can be any of the leaving groups mentioned above, but is preferably mesyl.

The N-alkylation according to process embodiment (d) can be carried out, for example, with an alkylating agent such as an alkyl halide or a dialkyl sulfate. Alternatively, the alkylation can be carried out reductively, for example, using formaldehyde and formic acid or by acylation and reduction, for example, with lithium aluminum hydride.

For the preparation of compounds of formula I in which $R^1$ is hydrogen according to process embodiment (e), a very reactive complex hydride, such as lithium aluminum hydride and DIBAH, can be used as the reducing agent. The reduction is preferably carried out in the presence of an inert organic solvent, such as ether, tetrahydrofuran, monoglyme, diglyme or toluene, at a temperature in the range of from 0° C. to 100° C.

The starting materials of formula II, insofar as they are racemic or achiral, are known or can be prepared in analogy to the preparation of the known representative compounds.

Salts, for example, the hydrochloride salts of the optically active compounds of formula II can be prepared, for example, by reacting a salt, for example, a hydrochloride, of an optically active alcohol of the formula

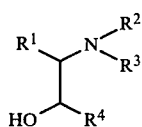

VIII wherein $R^1$, $R^2$, $R^3$ and $R^4$ are as previously described, in methylene chloride with thionyl chloride.

The optically active alcohols of formula VIII are known or can be obtained in analogy to the preparation of the known representative compounds.

The starting materials of formula III in which $R^1$ is hydrogen can be prepared by oxidizing an alcohol of the formula

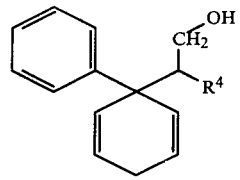

IX wherein $R^4$ is as previously described. The oxidation can be carried out by means of sulfur trioxide-pyridine complex in dimethylsulfoxide.

The starting materials of formula V in which $R^1$ is hydrogen can be prepared by reducing an ester of the formula

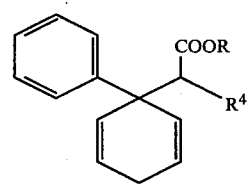

X wherein $R^4$ is as previously described and R is lower alkyl, to give an alcohol of formula IX and esterifying this alcohol.

The esters of formula X can be obtained by reacting biphenyl in the presence of lithium or calcium and ammonia with a chloroacetic acid ester of the formula

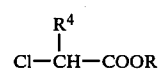

XI wherein R and $R^4$ are as previously described.

Starting materials of formula III in which $R^1$ is methyl can be prepared, for example, from starting materials of formula III in which $R^1$ is hydrogen by treatment with methylmagnesium iodide or bromide and oxidizing the resulting alcohol of the formula

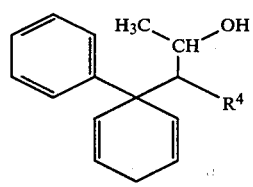

XII wherein $R^4$ is as previously described, with sulfur trioxide-pyridine complex in dimethylsulfoxide to give a starting material of formula III in which $R^1$ is methyl. Alcohols of formula XII can be esterified to give starting materials of formula V in which $R^1$ is methyl.

The amine starting materials of formula IV are known.

The amine starting materials of formula VI in which $R^1$ and $R^2$ each are hydrogen can be prepared by reacting biphenyl in the presence of lithium or calcium and ammonia with a compound of the formula

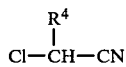

wherein $R^4$ is as previously described, and reducing the resulting nitrile of the formula

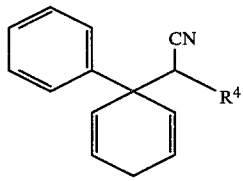

wherein $R^4$ is as previously described, with, for example, lithium aluminum hydride.

The amines of formula VI in which $R^1$ is hydrogen can also be prepared by reacting a compound of formula V with ammonia. The amines of formula VI in which $R^1$ is methyl or ethyl can be prepared by reacting a compound of formula V with monomethylamine or monoethylamine.

The amide starting materials of formula VII can be prepared, for example, by reacting biphenyl in the presence of lithium or calcium and ammonia with a compound of the formula

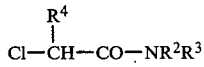

wherein $R^2$, $R^3$ and $R^4$ are as previously described.

Compounds of formula I which occur in the form of the racemates can be resolved into the antipodes according to known methods, for example, by racemate resolution with optically active acids.

Compounds of formula I can be converted into corresponding salts by treatment with inorganic or organic acids, the pharmaceutically compatible salts are particularly preferred. Examples of acids which form pharmaceutically compatible salts are hydrochloric acid, hydrobromic acid, nitric acid, sulfuric acid, phosphoric acid, tartaric acid, citric acid, maleic acid, ascorbic acid, formic acid, acetic acid, succinic acid, methanesulfonic acid, benzenesulfonic acid, p-toluenesulfonic acid, or the like.

The compounds of formula I and their acid addition salts have, as has been demonstrated in the known "writhing test" or "kaolin test", analgesic activity. The strength of the analgesic activity of the compounds of formula I is somewhat lower than that of codeine and propoxyphene, but stronger than that of aminophenazone and acetylsalicylic acid. In comparison with codeine and propoxyphene, the compounds of formula I are, however, distinguished by the fact that they have less undesirable side effects, particularly as to addiction liability, which is less or not present at all. The compounds of formula I can therefore be used in the control of pain. The dosage can vary within wide limits in any particular case depending upon the individual requirements. In the case of oral administration, a single dosage of 100–300 mg. and a daily dosage of 400–1200 mg. can be suitably utilized.

Of particular interest are compounds of formula I wherein:

(a) $R^1=R^4=H$ and $R^2=R^3=CH_3$(N,N-dimethyl-1-phenyl-2,5-cyclohexadien-1-ethylamine), (b) $R^1=R^4=H$ and $R^2=R^3=C_2H_5$(N,N-diethyl-1-phenyl-2,5-cyclohexadien-1-ethylamine); and (c) $R^1=CH_3$, $R^4=H$ and $R^2=R^3=CH_3$($\alpha$,N,N-trimethyl-1-phenyl-2,5-cyclohexadien-1-ethylamine).

The compound named under (a) is especially preferred.

The cyclohexadiene derivatives provided by the present invention can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions. They can, however, also be administered rectally, for example, in the form of suppositories; locally or percutaneously, for example, in the form of salves, creams, gels, solutions; or parenterally, for example, in the form of injectable solutions.

In the preparation of tablets, coated tablets, dragees and hard gelatin capsules, the cyclohexadiene derivatives can be processed with pharmaceutical inert, inorganic or organic excipients. Examples of excipients which can be utilized for tablets, dragees and hard gelatin capsules are lactose, maize starch or derivatives thereof, talc, stearic acid or its salts, and the like.

Suitable excipients for soft gelatin capsules are, for example, vegetable oils, waxes, fats, semi-solid and liquid polyols, and the like. Depending on the nature of the active ingredient no excipients are, however, generally required in the case of soft gelatin capsules.

Suitable excipients for the preparation of solutions and syrups are, for example, water, polyols, saccharose, invert sugar, glucose and the like.

Suitable excipients for injectable solutions are, for example, water, alcohols, polyols, glycerine, vegetable oils and the like.

Suitable excipients for suppositories or local or percutaneous administration forms are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

The following Examples further illustrate the invention. All temperatures are in degrees Centigrade, unless otherwise mentioned.

EXAMPLE 1

Preparation of N,N-dimethyl-1-phenyl-2,5-cyclohexadien-1-ethylamine maleate 15.4 g. of biphenyl are added while stirring in 300 ml. of absolute ether at −33° C. to 600 ml. of condensed, dry ammonia. Then, 1.53 g. of lithium wire (about 2 cm long pieces, de-greased with cyclohexane) are introduced within 15 minutes and the mixture is stirred for a further 1 hour. A solution of 23.7 g. of 2-chloro-N,N-dimethylethylamine in 100 ml. of absolute ether is then rapidly added dropwise. The mixture is stirred for a further 20 minutes and subsequently worked-up as follows:

11.8 g. of solid ammonium chloride are introduced and the ammonia is distilled off completely. 200 ml. of distilled water are added and the phases are separated. The aqueous phase is adjusted to a pH greater than 12 with sodium hydroxide and extracted twice with 200 ml. of ether. The organic phases are combined and extracted twice with 200 ml. of 2 N aqueous hydrochloric acid. The hydrochloric acid extracts are again adjusted to a pH greater than 12 and extracted twice with 200 ml. of ether. The ether extracts are dried with sodium chloride and with sodium sulfate, filtered and evaporated.

There is obtained in oil which, after two-fold bulb-tube distillation (89°–91° C./0.02 Torr), yields N,N-dimethyl-1-phenyl-2,5-cyclohexadien-1-ethylamine.

The product obtained is converted into the maleate with maleic acid in the usual manner (using acetone as the solvent) and the maleate is recrystallized from acetone/ether. The N,N-dimethyl-1-phenyl-2,5-cyclohexadien-1-ethylamine maleate (1:1) is dried for 3 hours at room temperature in a high vacuum and has a melting point of 130°–132° C.

EXAMPLE 2

Preparation of N,N-dimethyl-1-phenyl-2,5-cyclohexadien-1-ethylamine 23.1 g. of biphenyl in 200 ml. of ether are added to 300 ml. of condensed, dry ammonia and then 2.1 g. of lithium wire (about 2 cm long pieces, de-greased with cyclohexane) are subsequently added at −40° C. over a period of 15 minutes. The mixture is then held at boiling temperature (about −33° C.) for 2 hours. Subsequently, 7.2 g. of 2-chloro-N,N-dimethylethylamine hydrochloride are rapidly added portionwise at about −70° C. The mixture is again warmed to boiling temperature and held at this temperature for 0.5 hour. After the subsequent addition of ammonium chloride, distillation of the ammonia and aqueous working-up, an oily product is obtained. After purification by chromatography on a 20-fold amount of silica gel using methylene chloride/methanol (10:1) for the elution, the resulting N,N-dimethyl-1-phenyl-2,5-cyclohexadien-1-ethylamine is converted into the (1:1)-maleate as described in Example 1.

EXAMPLE 3

Preparation of α,N,N-trimethyl-1-phenyl-2,5-cyclohexadien-1-ethylamine 46.1 g. of biphenyl in 400 ml. of absolute ether are added at about −33° C. while stirring to 600 ml. of dry, condensed ammonia. 4.2 g. of lithium wire (about 2 cm long pieces, de-greased with cyclohexane) are then added at about −50° C. within 15 minutes. The mixture is held at boiling temperature for 2 hours. It is then cooled to about −70° C. and 15.8 g. of racemic 2-chloro-N,N,1-trimethylethylamine hydrochloride are added portionwise over a period of 10 minutes. The mixture is again warmed to boiling temperature (about −33° C.) and stirred at this temperature for 2 hours. 32 g. of ammonium chloride are then added and the ammonia is distilled off. Subsequently, the mixture is worked-up aqueous: the ether solution is washed with water. The aqueous phase is adjusted to a pH greater than 12 with sodium hydroxide solution and extracted further twice with ether. The ether phases are combined and extracted twice with 2 N aqueous hydrochloric acid. The acid extracts are again made alkaline and extracted with ether. The ether phases are dried, filtered and concentrated. There is obtained an oily product which, after chromatography on a 20-fold amount of silica gel using methylene chloride/methanol (10:1) as the solvent, yields α,N,N-trimethyl-1-phenyl-2,5-cyclohexadien-1-ethylamine. This product is dissolved in ether and converted with hydrogen chloride into the hydrochloride which is recrystallized from methylene chloride/ether. The product has a melting point of 158°–159° C.

EXAMPLE 4

Preparation of β,N,N-trimethyl-1-phenyl-2,5-cyclohexadien-1-ethylamine 15.4 g. of biphenyl in 300 ml. of absolute ether are added at about −33° C. while stirring to 600 ml. of dry, condensed ammonia. 1.72 g. of lithium wire (about 2 cm long pieces, de-greased with cyclohexane) are then introduced. The mixture is stirred for a further 1 hour. Then, a solution of 24.3 g. of 1-dimethylamino-2-chloropropane in 100 ml. of absolute ether is added. The mixture is stirred for a further 20 minutes and then worked-up as described in Example 1. Chromatography of the extract containing the amine on 500 g. of aluminum oxide (activity II) with methylene chloride yields β,N,N-trimethyl-1-phenyl-2,5-cyclohexadien-1-ethylamine which is converted with ethanolic hydrochloric acid into the hydrochloride and recrystallized from isopropanol. The product has a melting point of 204°–205° C.

EXAMPLE 5

Preparation of (S)-α,N,N-trimethyl-1-phenyl-2,5-cyclohexadien-1-ethylamine 28 g. of biphenyl in 300 ml. of absolute ether are added dropwise at about −33° C. while stirring to 360 ml. of dry, condensed ammonia. The mixture is cooled to about −50° C. and 2.5 g. of lithium wire (about 2 cm long pieces, de-greased with cyclohexane) are added over a period of 10 minutes. Then, the mixture is stirred at boiling temperature (about −33° C.) for 2 hours. 9.4 g. of (S)-2-chloro-N,N,1-trimethylethylamine hydrochloride are added portionwise at about −50° C. within about 3 minutes. The mixture is stirred at about −33° C. for 2 hours and subsequently worked-up. After adding ammonium chloride, distilling off of the ammonia, and aqueous working-up and chromatography in analogy to Example 3, there is obtained (S)-α,N,N-trimethyl-1-phenyl-2,5-cyclohexadien-1-ethylamine which is converted in the usual manner into the maleate. After crystallization from ether, the product has a melting point of 87°–90° C.

The (S)-2-chloro-N,N,1-trimethyl-ethylamine hydrochloride used as the starting material is prepared as follows:

12.4 g. of (S)-2-(dimethylamino)-1-propanol hydrochloride are dissolved in 100 ml. of methylene chloride and 25.3 ml. of thionyl chloride are added dropwise while cooling with ice within 0.5 hour. The mixture is stirred at room temperature for 3 hours and subsequently concentrated to dryness in vacuo. The thus-obtained crystalline residue is recrystallized from methylene chloride/ether. The resulting (S)-2-chloro-N,N,1-trimethyl-ethylamine hydrochloride has a melting point of 98°–102° C.

(R)-2-Chloro-N,N,1-trimethyl-ethylamine hydrochloride is prepared in the same manner from (R)-2-(dimethylamino)-1-propanol hydrochloride.

In an analogous manner to that previously described, from (R)-2-chloro-N,N,1-trimethylethylamine hydrochloride and biphenyl there is obtained (R)-α,N,N-trimethyl-1-phenyl-2,5-cyclohexadien-1-ethylamine maleate.

EXAMPLE 6

Preparation of crude α,N,N-trimethyl-1-phenyl-2,5-cyclohexadien-1-ethylamine hydrochloride 15.4 g. of biphenyl in 300 ml. of absolute ether are added at −33° C. while stirring to 600 ml. of dry, condensed ammonia. 1.67 g. of lithium wire (about 2 cm long pieces, de-greased with cyclohexane) are then introduced at −70° C. while stirring over a period of 15 minutes. The mixture is stirred at −33° C. for a further 1 hour. 26.0 g. of freshly distilled methyl choroacetate in 100 ml. of absolute ether are introduced at −70° C. in about 35 minutes, the dark red color of the mixture turning to yellow. Then, 13.0 g. of ammonium chloride are introduced and the ammonia is distilled off. 200 ml. of distilled water are added and the phases are separated. The ether phase is washed with 2 N aqueous hydrochloric acid and with 2 N aqueous sodium bicarbonate solution. The aqueous phases are re-extracted with ether and the combined ether phases are dried with sodium chloride and with sodium sulfate, filtered and concentrated completely. Distillation of the residue at 0.03 mmHg yields 1.5 g. of product. The fraction passing over at 89° C. contains methyl 1-phenyl-2,5-cyclohexadien-1-acetate.

A solution of 68.5 g. of methyl 1-phenyl-2,5-cyclohexadien-1-acetate in 250 ml. of absolute ether is added dropwise while stirring to a solution of 11.4 g. of lithium aluminum hydride in 1150 ml. of absolute ether. The mixture is stirred for 1 hour. 50 ml. of ethanol and subsequently 50 ml. of water are cautiously added. Suction filtration and washing with ether are then carried out. The phases are separated and the combined ether solutions are concentrated to dryness. There is obtained a crystallizing liquid which is recrystallized from benzene/hexane. The resulting 1-phenyl-2,5-cyclohexadien-1-ethanol has a melting point of 58°–59° C.

10 g. of the product obtained according to the preceding paragraph are dissolved in 70 ml. of dry dimethylsulfoxide. 44 ml. of triethylamine are added. Then, 24 g. of sulfur trioxide-pyridine complex in 100 ml. of dry dimethylsulfoxide are added dropwise while cooling with ice. After stirring at room temperature for 1 hour, the mixture is worked-up as follows: The mixture is poured into water and extracted twice with ether. The ether phases are washed with 3 N aqueous hydrochloric acid, washed neutral with water, dried, filtered and concentrated. There is obtained an oily product which is chromatographed on 200 g. of silica gel with petroleum ether/ether (3:1). There is obtained 1-phenyl-2,5-cyclohexadien-1-acetaldehyde in the form of an oily product. To 2.4 g. of magnesium shavings 14.2 g. of methyl iodide in 15 ml. of absolute ether are added dropwise. The mixture is heated to reflux for 1 hour, cooled and filtered over glass wool. The filtrate is added dropwise to a solution of 13 g. of 1-phenyl-2,5-cyclohexadien-1-acetaldehyde in 50 ml. of absolute ether. After heating to reflux for 3 hours, the mixture is worked-up as follows: The mixture is added to about 2 N aqueous ammonium chloride solution and extracted. The aqueous phase is re-extracted with ether. The combined organic phases are washed with water, dried with sodium sulfate, filtered and concentrated. The crude product is chromatographed on 260 g. of silica gel with petroleum ether/ether (1:1). There is obtained α-methyl-1-phenyl-2,5-cyclohexadien-1-ethanol as an oily product.

1 g. of the product obtained according to the preceding paragraph is dissolved in 10 ml. of dry dimethylsulfoxide. 3.9 ml. of triethylamine are added. Then, 2.3 g. of sulfur trioxide-pyridine complex in 7 ml. of dry dimethylsulfoxide are added dropwise while cooling with ice. After stirring at room temperature for 4 hours, the mixture is worked-up as follows: The mixture is poured into water and extracted twice with ether. The ether phases are washed with 3 N aqueous hydrochloric acid, washed neutral with water, dried, filtered and concentrated. The crude product is chromatographed on silica gel with petroleum ether/ether (1:1). There is obtained (1-phenyl-2,5-cyclohexadien-1-yl)-2-propanone as a colorless oily product.

To 50 ml. of methanol, 10 ml. of dimethylamine and 1 g. of molecular sieve 3 A are added dropwise at about −5° C. 10 ml. of 5 N methanolic hydrochloric acid and subsequently at 0° C. a solution of 5.3 g. of (1-phenyl-2,5-cyclohexadien-1-yl)-2-propanone in 20 ml. of methanol. 1.1 g. of sodium cyanoborohydride are then added at 0° C. and the mixture is stirred at room temperature for 4 days. The mixture is worked-up as follows: Ether and ice-water are added to the mixture and the phases are separated. The ether phase is extracted with dilute aqueous hydrochloric acid. The acid extracts are made alkaline with concentrated ammonia and extracted with ether. The combined ether phases are filtered and concentrated. There is obtained crude α,N,N-trimethyl-1-phenyl-2,5-cyclohexadien-1-ethylamine which is dissolved in ether, converted with hydrogen chloride into the hydrochloride and recrystallized from methylene chloride/ether. According to melting point and mixed melting point, the thus-obtained product is identical with that obtained in accordance with Example 3.

EXAMPLE 7

Preparation of crude N,N-dimethyl-1-phenyl-2,5-cyclohexadien-1-ethylamine 18.6 g. of methanesulfonyl chloride are added dropwise while stirring and cooling with ice to a solution of 27 g. of 1-phenyl-2,5-cyclohexadien-1-ethanol in 270 ml. of absolute pyridine. After stirring at room temperature for 3 hours, about 250 ml. of water are added. The separated product is filtered off under suction, washed with water and dried. The crude product is recrystallized from benzene/hexane, there being obtained methansulfonic acid 2-(1-phenyl-2,5-cyclohexadien-1-yl)-ethyl ester as colorless crystals of melting point 64°–65° C.

100 g. of the foregoing ester are dissolved in 600 ml. of toluene. 70 ml. (about three equivalents) of condensed dimethylamine are added at −10° C. and then the mixture is heated at 150° C. in a pressure vessel for 16 hours. The mixture is worked-up as follows: The toluene solution is washed with water and concentrated completely. The resulting oil is dissolved in benzene and extracted with 3 N aqueous hydrochloric acid. The aqueous phase is made alkaline with concentrated ammonia and extracted with ether. The combined ether extracts are washed with water, dried with sodium sulfate, filtered and concentrated. There is obtained crude N,N-dimethyl-1-phenyl-2,5-cyclohexadien-1-ethylamine which is converted into the (1:1)-maleate in the usual manner.

EXAMPLE 8

Preparation of N-methyl-1-phenyl-2,5-cyclohexadien-1-ethylamine hydrochloride

Methanesulfonic acid 2-(1-phenyl-2,5-cyclohexadien-1-yl)-ethyl ester is reacted with methylamine by an analogous procedure to that described in Example 7. The crude product obtained is converted in the usual manner into the hydrochloride which is recrystallized from isopropanol. There is obtained N-methyl-1-phenyl-2,5-cyclohexadien-1-ethylamine hydrochloride having a melting point of 172°–173° C.

EXAMPLE 9

Preparation of N,N-diethyl-1-phenyl-2,5-cyclohexadien-1-ethylamine hydrochloride 87 g. of methanesulfonic acid 2-(1-phenyl-2,5-cyclohexadien-1-yl)-ethyl ester are dissolved in 600 ml. of toluene. 95 ml. (about 3 equivalents) of diethylamine are added and then the mixture is heated at 150° C. in a pressure vessel for 16 hours. The workingup is carried out as described in the second part of Example 7. There is obtained crude N,N-diethyl-1-phenyl-2,5-cyclohexadien-1-ethylamine which is dissolved in ether and converted with hydrogen chloride into the hydrochloride. After recrystallization from methylene chloride/ether, there is obtained the hydrochloride having the melting point of 134°–136° C.

EXAMPLE 10

Preparation of β,N,N-trimethyl-1-phenyl-2,5-cyclohexadien-1-ethylamine hydrochloride 15.4 g. of biphenyl in 130 ml. of absolute ether are added dropwise at −33° C. under argon while stirring to 600 ml. of condensed ammonia distilled over sodium. Then, the mixture is cooled to −70° C. and 2 g. of lithium wire (about 2 cm long pieces, de-greased with cyclohexane) are introduced within 15 minutes. The mixture is stirred at −70° C. for 1 hour and 26.3 ml. of freshly distilled methyl 2-chloropropionate in 40 ml. of absolute ether are added dropwise over a period of 35 minutes. After completion of the addition, 13.4 g. of solid ammonium chloride are added. After distilling off the ammonia, 170 ml. of water are added and the mixture is extracted with ether. The organic phase is washed with dilute hydrochloric acid and subsequently with aqueous sodium carbonate solution, dried with sodium sulfate, filtered and concentrated. The crude product obtained is chromatographed on 1.3 kg. of silica gel with ether/petroleum ether (1:2). There is obtained methyl 2-(1-phenyl-2,5-cyclohexadien-1-yl)-propionate as an oily product.

0.76 g. of lithium aluminum hydride is placed in 20 ml. of absolute ether. 2.42 g. of methyl 2-(1-phenyl-2,5-cyclohexadien-1-yl)-propionate in 20 ml. of absolute ether are added dropwise thereto. After stirring at room temperature for 5 hours, the mixture is worked-up as follows: The mixture is treated with ethyl acetate and water, filtered under suction and the organic phase is separated from the aqueous phase. The organic phase is dried with sodium sulfate, filtered and evaporated. The crude product obtained is chromatographed on 80 g. of silica gel with ether/petroleum ether (1:2), oily β-methyl-1-phenyl-2,5-cyclohexadien-1ethanol being obtained.

5 g. of the product obtained according to the preceding paragraph are dissolved in 150 ml. of dry dimethylsulfoxide and treated with 18.8 ml. of triethylamine. 11.4 g. of sulfur trioxide-pyridine complex in 100 ml. of dimethylsulfoxide are then added dropwise at room temperature. After 2 hours at room temperature, the mixture is worked-up as follows: The mixture is poured on to ice-water and extracted with ether. The organic phases are washed with dilute aqueous hydrochloric acid, washed neutral with water, dried with magnesium sulfate, filtered and concentrated. There is obtained β-methyl-1-phenyl-2,5-cyclohexadien-1-acetaldehyde in the form of an oily product.

2.8 ml. of 11.2 N methanolic hydrochloric acid are added dropwise at 0° C. to 50 ml. of methanol, 6.2 ml. of dimethylamine and 1 spatula of molecular sieve 3 A. 3.3 g. of β-methyl-1-phenyl-2,5-cyclohexadien-1-acetaldehyde in a small amount of methanol are then added dropwise at 0° C. and then 0.51 g. of sodium cyanoborohydride is added. The mixture is stirred at room temperature for 4 days and then worked-up as follows: The mixture is treated with ether and bicarbonate and extracted. The organic phase is extracted with dilute hydrochloric acid. The acid extract is made alkaline with concentrated ammonia and extracted in ether. The combined organic phases are dried, filtered and concentrated completely. The crude product obtained is chromatographed on silica gel with ether/trimethylamine (10:1), the resulting product being dissolved in ether and converted into the hydrochloride by treatment with hydrogen chloride. After crystallization from methylene chloride/ether, there is obtained β,N,N-trimethyl-1-phenyl-2,5-cyclohexadien-1-ethylamine hydrochloride having a melting point of 198°–199° C.

EXAMPLE 11

Preparation of N,N-diethyl-1-phenyl-2,5-cyclohexadien-1-ethylamine hydrochloride A solution of 30.8 g. of biphenyl in 600 ml. of absolute ether is added dropwise to 1.2 liters of condensed, dry ammonia. 3.47 g. of lithium wire (about 2 cm long pieces, de-greased with cyclohexane) are then added portionwise and the mixture is stirred for 1 hour. 73.3 g. of N,N-diethyl-chloroacetamide in 200 ml. of absolute ether are then added dropwise. After a further 0.25 hour, the mixture is worked-up as follows: The mixture is treated with 26.2 g. of ammonium chloride and the ammonia is distilled off. After the addition of water, the phases are separated. The organic phase is washed with dilute hydrochloric acid and subsequently with 2 N aqueous sodium carbonate solution, dried over sodium sulfate, filtered and concentrated to dryness. The resulting residue is purified by chromatography over Alox and distilled (boiling point 150°–152° C.; 0.4 mmHg). The resulting N,N-diethyl-1-phenyl-2,5-cyclohexadien-1-acetamide is used in the next step without additional purification.

7.6 g. of lithium aluminum hydride in absolute ether are added dropwise to an ethereal solution of 27 g. of N,N-diethyl-1-phenyl-2,5-cyclohexadien-1-acetamide.

After stirring for 1 hour, 15 ml. of ethanol and subsequently 15 ml. of water are added. The ether solution is decanted off and extracted with dilute hydrochloric acid. The acid extract is made alkaline and extracted with ether. The ether phases are dried and concentrated. The oil obtained is distilled (boiling point 107°–110° C.; 0.1 mmHg). The hydrochloride of N,N-diethyl-1-phenyl-2,5-cyclohexadien-1-ethylamine prepared in the usual manner has a melting point of 133°–134° C. after crystallization from isopropanol/ether and absolute ethanol/ether.

EXAMPLE 12

Preparation of α,N,N-trimethyl-1-phenyl-2,5-cyclohexadien-1-ethylamine hydrochloride 8 g. of α-methyl-1-phenyl-2,5-cyclohexadien-1-ethanol are dissolved in 50 ml. of pyridine and 6.4 g. of mesyl chloride are added dropwise at 0°–5° C. After stirring at room temperature for 2 hours, the mixture is worked-up as follows: The mixture is treated with ice-water and extracted with ether. The ether phase is washed with 3 N aqueous hydrochloric acid, then washed neutral, dried and concentrated. The crude product obtained is chromatographed on 100 g. of silica gel with ether/petroleum ether (1:1). There is obtained an oily product which crystallizes in the cold. After crystallization from methylene chloride/hexane, there is obtained methanesulfonic acid 1-methyl-2-(1-phenyl-2,5-cyclohexadien-1-yl)-ethyl ester having a melting point of 51°–53° C.

1.1 ml. (about 3 equivalents) of condensed dimethylamine are added at −10° C. to 1.5 g. of methanesulfonic acid 1-methyl-2-(1-phenyl-2,5-cyclohexadien-1-yl)-ethyl ester in 5 ml. of toluene. The mixture is then held at 150° C. in a pressure vessel for 16 hours. Subsequently, the mixture is cooled down and worked-up as follows: The toluene phase is washed with water, concentrated, treated with ether and 3 N aqueous hydrochloric acid and shaken out. The aqueous extract is made basic with concentrated ammonia and extracted with ether. There is obtained an oily residue which is chromatographed on a thick-layer plate with methylene chloride/methanol (10:1). There is obtained α,N,N-trimethyl-1-phenyl-2,5-cyclohexadien-1-ethylamine which is converted in the usual manner into the hydrochloride.

EXAMPLE 13

Preparation of β,N-dimethyl-1-phenyl-2,5-cyclohexadien-1-ethylamine 23 g. of methyl 1-phenyl-2,5-cyclohexadien-1-acetate are dissolved in 250 ml. of dry tetrahydrofuran and cooled to about −70° C. 1 g. of 18-crown-6 ether, 19 g. of potassium tert.butylate and 28 ml. of methyl iodide are then added. The mixture is stirred at −70° C. overnight and then worked-up as follows: The mixture is poured on to ice-water and extracted with ether. The organic phases are washed with water, dried with magnesium sulfate, filtered and concentrated completely. The resulting oil is filtered over a silica gel column. The thus-obtained product, methyl 2-(1-phenyl-2,5-cyclohexadien-1-yl)-propionate, is used in the next step without further purification.

3 g. of lithium aluminum hydride are placed in 100 ml. of dry ether and 18.9 g. of the product obtained as described in the preceding paragraph are added dropwise thereto in 80 ml. of ether. After 2 hours at room temperature, the mixture is worked-up as follows: The excess lithium aluminum hydride is destroyed with alcohol and subsequently with water. After filtration, the phases are separated and the ether phase is washed with water, dried with magnesium sulfate, filtered and concentrated. There is obtained a clear oil which is chromatographed on silica gel with petroleum ether/ether (1:1). There is obtained β-methyl-1-phenyl-2,5-cyclohexadien-1-ethanol as an oily product.

15 g. of the product obtained as described in the preceding paragraph are dissolved in 200 ml. of pyridine and 8.8 ml. of methanesulfonyl chloride are dropped in. After stirring at room temperature for 6 hours, the mixture is worked-up as follows: The mixture is treated with ether and washed with water, 3 N aqueous hydrochloric acid and again with water, dried over sodium sulfate, filtered and concentrated to dryness. The crude product obtained is chromatographed on silica gel with petroleum ether/ether (1:2), oily methanesulfonic acid 2-(1-phenyl-2,5-cyclohexadien-1-yl)-propyl ester being obtained.

9.4 g. of the foregoing ester are dissolved in 8 ml. of toluene. 4.1 ml. (about 3 equivalents) of condensed methylamine are added at −10° C. The mixing is then held at 150° C. in a pressure vessel for 24 hours. Subsequently, the mixture is again treated with 8.2 ml. of methylamine and the resulting mixture is held at 150° C. for a further 24 hours. Subsequently, the mixture is concentrated, treated with ether and 3 N hydrochloric acid and extracted. After suction filtration of the separated crystals, the aqueous phase is made alkaline and extracted with methylene chloride. The crystal fraction is likewise treated with methylene chloride and aqueous sodium hydroxide. The combined methylene chloride phases are washed neutral with water, dried with sodium sulfate, filtered and concentrated. The oily product obtained is chromatographed on 120 g. of Alox (neutral) with methylene chloride/methanol (10:1). There is obtained β,N-dimethyl-1-phenyl-2,5-cyclohexadien-1-ethylamine. The hydrochloride prepared in the customary manner has a melting point above 250° C.

EXAMPLE 14

Preparation of (N,N-dimethyl-1-phenyl-2,5-cyclohexadien-1-ethylamine) maleate 600 ml. of ammonia distilled over sodium are placed under argon at −33° C. 15.4 g. of biphenyl in 130 ml. of ether are then added dropwise while stirring. After cooling to −70° C., 2 g. of lithium wire (about 2 cm long pieces, de-greased with cyclohexane) are added over a period of 10 minutes. After stirring at −70° C. for 1 hour, 18.6 g. of freshly distilled chloroacetonitrile in 45 ml. of absolute ether are added dropwise over a period of 45 minutes. Subsequently, 13.4 g. of solid ammonium chloride are added and the ammonia is distilled off. The mixture is poured on to ice-water and extracted with ether. The organic phase is washed with dilute hydrochloric acid and subsequently with aqueous sodium carbonate solution, dried, filtered and concentrated. The crude product is chromatographed on 1 kg. of silica gel with ether/petroleum ether (1:2). Pure 1-phenyl-2,5-cyclohexadien-1-acetonitrile is obtained.

0.68 g. of aluminum trichloride and 0.24 g. of lithium aluminum hydride are placed in 8 ml. of absolute ether. 1 g. of 1-phenyl-2,5-cyclohexadien-1-acetonitrile in 5 ml. of absolute ether is added dropwise while stirring.

After stirring at room temperature for 2 hours, the mixture is worked-up as follows: The mixture is treated with 1 ml. of water and 25 ml. of 3 N aqueous sodium hyroxide, filtered under suction and the filter rinsed with ether. After separating the phases, the organic phase is dried over sodium sulfate, filtered and concentrated to dryness. The crude product obtained is chromatographed on 50 g. of Alox (neutral), educt being first of all eluted with ether and then end product being eluted with methylene chloride/methanol (10:1). There is obtained 1-phenyl-2,5-cyclohexadien-1-ethylamine as an oily product. 3 g. of this product are converted in the usual manner into the hydrochloride which, after recrystallization from methylene chloride/ether, has a melting point of 170°–172° C.

4 g. of 1-phenyl-2,5-cyclohexadien-1-ethylamine hydrochloride are placed in 100 ml. of absolute methanol. After the addition of 3.3 g. (6.5 equivalents) of p-formaldehyde, 1 g. (about 1 equivalent) of sodium cyanoborohydride and 5 g. of molecular sieve 3A, the mixture is stirred at room temperature overnight and subsequently worked-up as follows: The mixture is poured into aqueous 3 N hydrochloric acid, stirred for 10 minutes, made basic with concentrated aqueous ammonia, extracted with ethyl acetate, washed with water, dried with sodium sulfate and filtered. There is obtained an oily product which is chromatographed on 80 g. of silica gel with methylene chloride/methanol (10:1). The yellow oil obtained (N,N-dimethyl-1-phenyl-2,5-cyclohexadien-1-ethylamine) is converted in the customary manner into the (1:1)-maleate which has a melting point of 129°–131° C.

EXAMPLE 15

Preparation of
N,N-dimethyl-1-phenyl-2,5-cyclohexadien-1-ethylamine maleate

To 6.4 g. (8.6 equivalents) of dimethylamine and 5 g. of molecular sieve 3A in 50 ml. of absolute methanol are added dropwise at 0° C. 6.6 ml. of 5 N methanolic hydrochloric acid (2 equivalents) and subsequently 3.3 g. of 1-phenyl-2,5-cyclohexadien-1-acetaldehyde in 10 ml. of absolute methanol. After the addition of 0.75 g. (0.72 equivalents) of sodium cyanioborohydride, the mixture is stirred at room temperature for 5 days. The mixture is treated with ice-water and ether and extracted with 3 N sodium hydrocloric acid. The hydrochloric acid extracts are made basic with concentrated aqueous ammonia and extracted with ether. The ether phase is dried with sodium sulfate, filtered, evaporated and chromatographed on Alox neutral. The thus-obtained N,N-dimethyl-1-phenyl-2,5-cyclohexadien-1-ethylamine is converted as usual into the (1:1)-maleate which has a melting point of 128°–130° C.

EXAMPLE 16

Preparation of
α,N-dimethyl-1-phenyl-2,5-cyclohexadien-1-ethylamine hydrochloride To 11.5 ml. (about 6 equivalents) of methylamine and 10 g. of molecular sieve 3A in 200 ml. of absolute methanol are added dropwise at 0° C. 17.8 ml. of 5 N methanolic hydrochloric acid (2 equivalents) and subsequently 9.4 g. of (1-phenyl-2,5-cyclohexadien-1-yl)-2-propanone in a small amount of methanol. After the addition of 1.95 g. (0.75 equivalent) of sodium cyanoborohydride, the mixture is stirred at room temperature for 5 days. The mixture is worked-up as follows: The mixture is treated with ice-water and ether and extracted with 3 N aqueous hydrochloric acid. The hydrochloric acid extracts are made basic with concentrated aqueous ammonia and extracted with ether. The ether phase is dried with sodium sulfate, filtered and evaporated. The crude product obtained is chromatographed on silica gel with methylene chloride/methanol (10:1). There is obtained α,N-dimethyl-1-phenyl-2,5-cyclohexadien-1-ethylamine in the form of an oily product. This is converted as usual into the hydrochloride which, after crystallization from methylene chloride/ether, has a melting point of 155°–158° C.

EXAMPLE 17

Preparation of
α-methyl-N-ethyl-1-phenyl-2,5-cyclohexadien-1-ethylamine hydrochloride To 5.3 g. (about 8 equivalents) of ethylamine and 10 g. of molecular sieve 3A in 100 ml. absolute methanol are added at 0° C. 5.6 ml. of 5 N methanolic hydrochloric acid (2 equivalents) and then 3 g. of (1-phenyl-2,5-cyclohexadien-1-yl)-2-propanone in a small amount of absolute methanol. 0.63 g. (0.7 equivalent) of sodium cyanoborohydride is then added and the mixture is stirred at room temperature for 5 days. The mixture is worked-up in exactly the same manner as described in Example 16. The crude product is chromatographed on silica gel with methylene chloride/methanol (10:1). There is obtained α-methyl-N-ethyl-1-phenyl-2,5-cyclohexadien-1-ethylamine as an oily product. This product is converted as usual into the hydrochloride which, after crystallization from methylene chloride/ether, has a melting point of 151°–153° C.

EXAMPLE 18

Preparation of
α-methyl-N,N-diethyl-1-phenyl-2,5-cyclohexadien-1-ethylamine hydrochloride 1.5 g. of α-methyl-N-ethyl-1-phenyl-2,5-cyclohexadien-1-ethylamine are dissolved in a mixture of 10 ml. of acetic acid anhydride and 8 ml. of pyridine and left to stand at room temperature overnight. Then, the mixture is stirred for 2 hours with 2 N aqueous potassium bicarbonate solution and subsequently extracted with ether. The ether phase is washed with dilute aqueous hydrochloride acid and then with water, dried with sodium sulfate, filtered and concentrated to dryness. The crude product obtained is chromatographed on silica gel with ether. There is obtained N-ethyl-N-[1-methyl-2-(1-phenyl-2,5-cyclohexadien-1-yl)ethyl]-acetamide in the form of an oily product.

0.266 g. of lithium aluminum hydride is placed in 10 ml. of tetrahydrofuran. After the addition of 1 g. of N-ethyl-N-[1-methyl-2-(1-phenyl-2,5-cyclohexadien-1-yl)ethyl]-acetamide in 10 ml. of tetrahydrofuan, the mixture is stirred at room temperature for 7 hours. Subsequently, excess lithium aluminum hydride is destroyed by the addition of ethyl aceate and of water. The mixture is filtered and the filter is rinsed with ether. After separation of the phases, the organic phase is dried with sodium sulfate, filtered and concentrated completely. The crude product is chromatographed on 60 g. of Alox neutral with ethyl acetate. There is obtained α-methyl-N,N-diethyl-1-phenyl-2,5-cyclohexadien-1-ethylamine in the form of an oily product. This is converted as usual into the hydrochloride which, after

EXAMPLE 19

Preparation of
β-methyl-N,N-diethyl-1-phenyl-2,5-cyclohexadien-1-ethylamine hydrochloride 8 g. of methanesulfonic acid 2-(1-phenyl-2,5-cyclohexadien-1-yl)-propyl ester are dissolved in 10 ml. of toluene. 8.4 ml. (about 3 equivalents) of condensed diethylamine are added at −10° C. The mixture is subsequently held at 150° C. in a pressure vessel for 25 hours. After cooling, the toluene phases is washed with water, concentrated, treated with ether and 3 N aqueous hydrochloric acid and extracted. The aqueous phase is made basic with concentrated aqueous ammonia and extracted with ether. The combined ether phases are dried over sodium sulfate, filtered and concentrated completely. There is obtained an oily product which is chromatographed on silica gel with methylene chloride/methanol (10:1). There is obtained β-methyl-N,N-diethyl-1-phenyl-2,5-cyclohexadien-1-ethylamine as an oily product. This product is converted as usual into the hydrochloride which, after recrystallization from ethanol/ether, has a melting point of 132°–137° C.

EXAMPLE 20

Preparation of
α-methyl-N,N-diethyl-1-phenyl-2,5-cyclohexadien-1-ethylamine hydrochloride To 27.5 ml. (about 6 equivalents) of diethylamine and 10 g. of molecular sieve 3A in 200 ml. of methanol are added at 0° C. 17.6 ml. of 5 N methanolic hydrochloric acid (2 equivalents) and then 9.4 g. of (1-phenyl-2,5-cyclohexadien-1-yl)-2-propanone in a small amount of methanol and finally 1.95 g. (0.7 equivalents) of sodium cyanoborohydride. The mixture is stirred at room temperature for 5 days and then worked-up in exactly the same manner as described in Example 16. There is obtained an oily residue which is chromatographed on a silica gel thick-layer plate with ethyl acetate/triethylamine (15:1). Two products are scratched off and eluted with methylene chloride/methanol (4:1). The product of RF 0.32 is α-methyl-N-ethyl-1-phenyl-2,5-cyclohexadien-1-ethylamine. The other product (RF 0.54) is the desired product, namely, α-methyl-N,N-diethyl-1-phenyl-2,5-cyclohexadien-1-ethylamine. This is converted as usual into the hydrochloride and recrystallized from methylene chloride/ether. According to melting point and mixed melting point, the product is identical with that obtained in accordance with Example 18.

EXAMPLE 21

Preparation of
N,N-dimethyl-1-phenyl-2,5-cyclohexadien-1-ethylamine maleate 46 g. of biphenyl in 400 ml. of ether are added dropwise at −33° C. under argon to 600 ml. of ammonia distilled over sodium. After cooling to −50° C., 12 g. of granulated calcium are added within 15 minutes. The solution is green-yellow and finally dark red to black. The solution is stirred at −33° C. for 2 hours and then cooled to −70° C. 14.4 g. of 2-chloro-N,N-dimethylethylamine hydrochloride are added to the mixture within 5 minutes. After stirring at −33° C. for 2 hours, the mixture is again cooled to −70° C. and 32 g. of ammonium chloride are added. The ammonia is distilled off overnight. The mixture is treated with 400 ml. of water and then made strongly basic by the addition of 28% aqueous sodium hydroxide. After filtration, the phases are separated and the organic phase is extracted with 3 N aqueous hydrochloric acid. The aqueous-acid extract is made basic with sodium hydroxide and extracted with ether. The ether phase is dried with sodium sulfate, filtered and concentrated to dryness. There is obtained an oily product which is chromatographed on 200 g. of silica gel with methylene chloride/methanol (10:1). The pure N,N-dimethyl-1-phenyl-2,5-cyclohexadien-1-ethylamine obtained is converted as usual into the (1:1)-maleate. The maleate obtained melts at 128°–130° C.

The following Examples illustrate pharmaceutical preparations containing cyclohexadiene derivatives provided by the present invention:

Example A

Hard gelatin capsule:

(a) Ingredients

| | |
|---|---|
| N,N-Dimethyl-1-phenyl-2,5-cyclohexadien-1-ethylamine maleate | 100.0 mg. |
| Lactose (crystalline) | 102.0 mg. |
| Maize starch (white) | 45.0 mg. |
| Talc | 10.4 mg. |
| Magnesium stearate | 2.6 mg. |
| | 260.0 mg. |

(b) Manufacture:

N,N-dimethyl-1-phenyl-2,5-cyclohexadien-1-ethylamine maleate is mixed with the maize starch, talc and magnesium stearate, the mixture is sieved, treated with the lactose, mixed and again sieved. The powder mixture obtained is filled into capsules of size No. 1.

Example B

Tablet:

(a) Ingredients:

| | |
|---|---|
| N,N-Dimethyl-1-phenyl-2,5-cyclohexadien-1-ethylamine maleate | 300.0 mg. |
| Lactose(crystalline) | 75.0 mg. |
| Maize starch(white) | 60.0 mg. |
| Primojel$^R$ | 12.0 mg. |
| Magnesium stearate | 3.0 mg. |
| | 450.0 mg. |

(b) Manufacture:

The N,N-dimethyl-1-phenyl-2,5-cyclohexadien-1-ethylamine maleate is mixed with the lactose and a part of the maize starch, the mixture is processed with a maize starch-water paste, granulated, dried and sieved. The granulate obtained is mixed with the Primojel ® and magnesium stearate and pressed to tablets weighing 450 mg.

We claim:

1. A compound of the formula

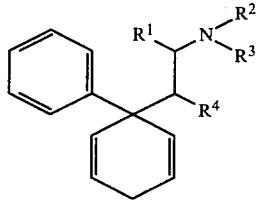

wherein $R^1$ is hydrogen or methyl, $R^2$ is hydrogen, methyl or ethyl, $R^3$ is methyl or ethyl and $R^4$ is hydrogen or methyl; provided that at least one of $R^1$ and $R^4$ is hydrogen; a pharmaceutically acceptable acid addition salt thereof, or an optically active antipode of a compound of formula I which has an asymmetric carbon atom.

2. A compound in accordance with claim 1, N,N-dimethyl-1-phenyl-2,5-cyclohexadien-1-ethylamine or a pharmaceutically compatible acid addition salt thereof.

3. A compound in accordance with claim 1, α,N,N-trimethyl-1-phenyl-2,5-cyclohexadien-1-ethylamine, β,N,N-trimethyl-1-phenyl-2,5-cyclohexadien-1-ethylamine, N-methyl-1-phenyl-2,5-cyclohexadien-1-ethylamine, N,N-diethyl-1-phenyl-2,5-cyclohexadien-1-ethylamine, α,N-dimethyl-1-phenyl-2,5-cyclohexadien-1-ethylamine, α-methyl-N-ethyl-1-phenyl-2,5-cyclohexadien-1-ethylamine, α-methyl-N,N-diethyl-1-phenyl-2,5-cyclohexadien-1-ethylamine, β,N-dimethyl-1-phenyl-2,5-cyclohexadien-1-ethylamine, β-methyl-N,N-diethyl-1-phenyl-2,5-cyclohexadien-1-ethylamine, or a pharmaceutically compatible acid addition salt thereof.

4. A pharmaceutical composition comprising a compound of the formula

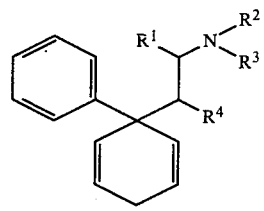

wherein $R^1$ is hydrogen or methyl, $R^2$ is hydrogen, methyl or ethyl, $R^3$ is methyl or ethyl and $R^4$ is hydrogen or methyl; provided that at least one of $R^1$ and $R^4$ is hydrogen, a pharmaceutically acceptable acid addition salt thereof, or an optically active antipode of a compound of formula I which has an asymmetric carbon atom, and inert pharmaceutical carrier material.

* * * * *